US00PP24697P3

(12) United States Plant Patent
Brazelton et al.

(10) Patent No.: US PP24,697 P3
(45) Date of Patent: Jul. 29, 2014

(54) BLUEBERRY PLANT NAMED 'TOP SHELF'

(50) Latin Name: ***Vaccinium corymbosum* hybrid**
Varietal Denomination: Top Shelf

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 150 days.

(21) Appl. No.: 13/385,903

(22) Filed: Mar. 12, 2012

(65) Prior Publication Data

US 2013/0239261 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

(56) References Cited

U.S. PATENT DOCUMENTS

PP15,103 P3 8/2004 Hancock

OTHER PUBLICATIONS

Retrieved from the internet at <http://tess2.uspto.gov/bin/showfield?f=doc&state=4803:lm5586.5.3> 2 pp.*
Brevis, PA et al., "Impact of Wide Hybridization on Highbush Blueberry Breeding," *J. Amer. Soc. Hort. Sci.*, 2008, 133(3):427-437.

* cited by examiner

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'Top Shelf' is provided. 'Top Shelf' is a commercial variety intended for the hand harvest market. The variety has jumbo-sized sky-blue fruit with excellent flavor. 'Top Shelf' ripens mid-season, and holds up well in storage trials. The plant is vigorous, with an upright, vase shaped growth habit, and has an estimated chilling requirement of 700 to 1,000 hours.

3 Drawing Sheets

Latin name of the family, genus and species: Family—Ericaceae. Genus—*Vaccinium.* Species—*corymbosum* hybrid.

Variety denomination: The new blueberry plant claimed is of the variety denominated 'Top Shelf.'

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry known as a *Vaccinium corymbosum* hybrid referred to as 'Top Shelf,' as herein described and illustrated.

The new blueberry plant variety 'Top Shelf' was selected in Lowell, Oreg. in 2007 'Top Shelf' is a commercial variety intended for the hand harvest market. The variety has jumbo-sized sky-blue fruit with excellent flavor. 'Top Shelf' ripens mid-season, approximately 2 to 3 weeks later than 'Duke,' and holds up well in storage trials. The plant is vigorous, with an upright vase shaped growth habit, and has an estimated chilling requirement of 700 to 1,000 hours.

Pedigree and History: The new blueberry plant originated from a cross of 'Magnolia' (female parent, unpatented) by 'Draper' (pollen parent, U.S. Plant Pat. No. 15,103). The new blueberry plant variety 'Top Shelf' has been planted in replicated trials since 2008.

The new variety can be compared to commercial variety 'Duke' in that 'Top Shelf' ripens 2 to 3 weeks later and has larger fruit.

The new variety can be compared to the pollen parent 'Draper' in that 'Top Shelf' is more vigorous, has larger fruit and a more appealing flavor.

The new blueberry plant variety 'Top Shelf' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Top Shelf' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'Top Shelf':

1. Jumbo-sized fruit with excellent flavor.
2. Vigorous plant with upright, vase shaped growth habit.
3. Excellent performance in storage trials.

BRIEF DESCRIPTION OF THE DRAWINGS

The accompanying photographic illustration shows typical specimens in full color of the foliage and fruit of the new variety 'Top Shelf.' The colors are a nearly true as is reasonably possible in a color representation of this type.

BOTANICAL DESCRIPTION

Figure 1:
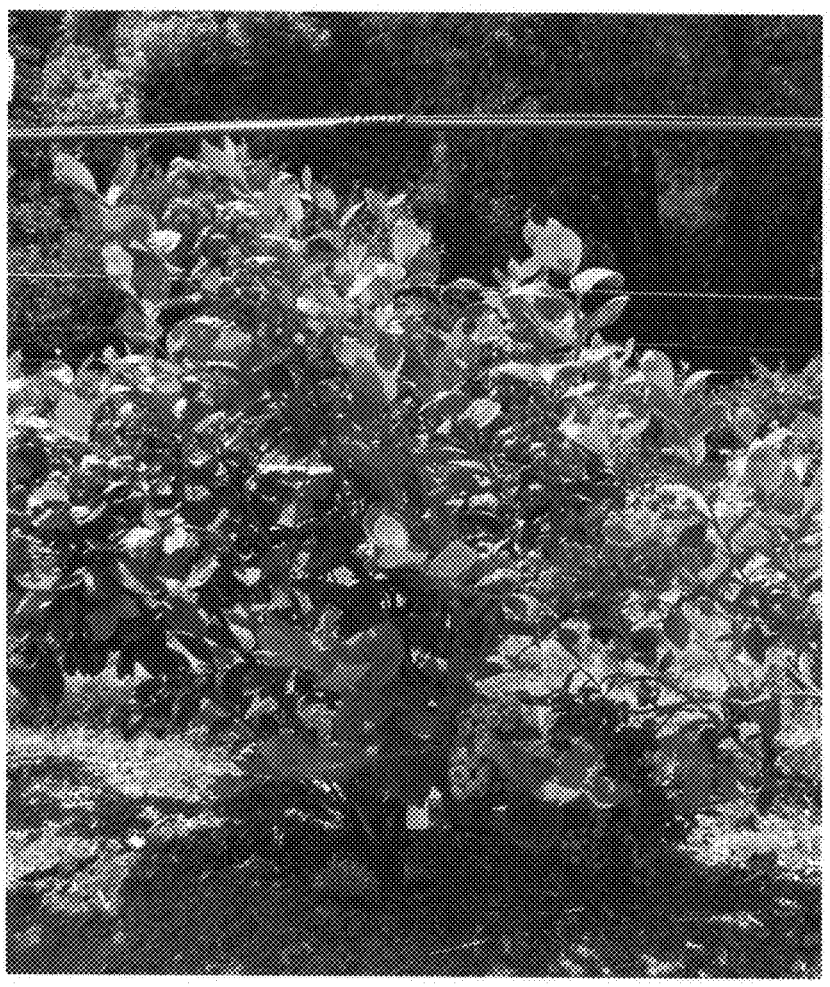
FIG. 1 is a photograph of the new variety 'Top Shelf,' highlighting the plant's upright growth habit and vigorous nature.
Figure 2:
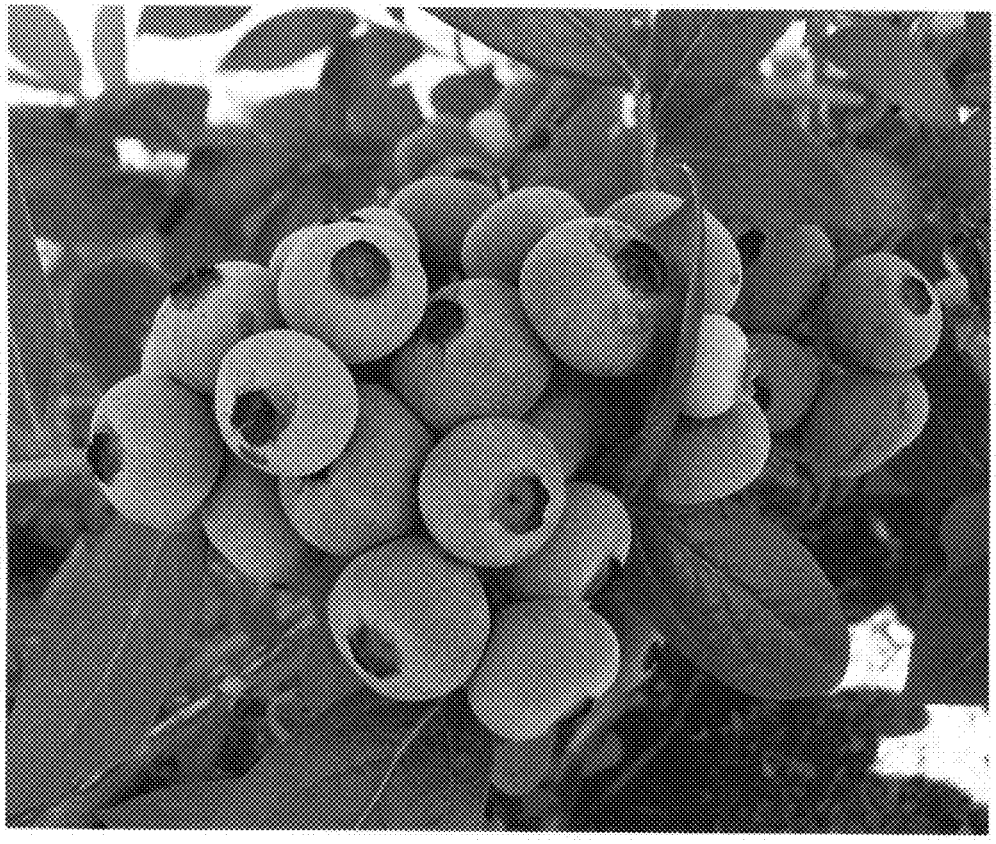
FIG. 2 is a photograph of the fruit of the new variety 'Top Shelf,' highlighting the jumbo-sized berries.
Figure 3:
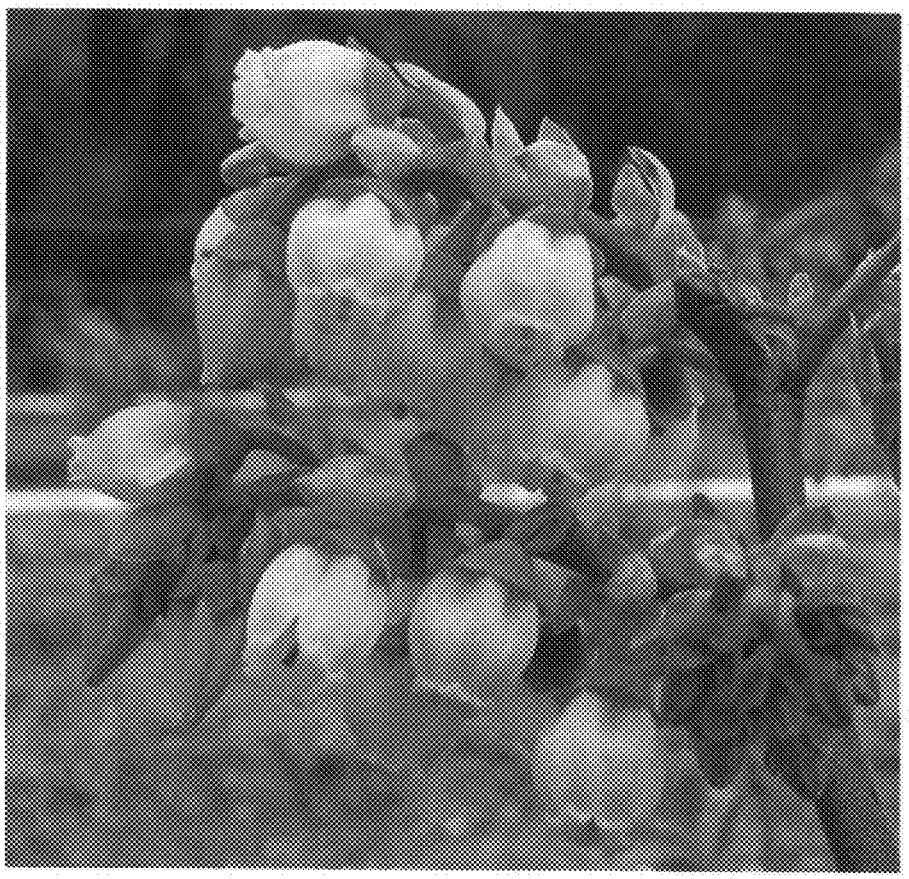
FIG. 3 is a photograph of the flowers of the new variety 'Top Shelf.'

The following detailed description sets forth the distinctive characteristics of 'Top Shelf.' The data which defines these characteristics was collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:
- *a. Family.*—Ericaceae.
- *b. Genus.*—*Vaccinium.*
- *c. Species.*—*corymbosum* hybrid.
- *d. Common name.*—Highbush Blueberry.

Parentage:
- *Female parent.*—'Magnolia' (unpatented).
- *Male parent.*—'Draper' (U.S. Plant Pat. No. 15,103).

Market class: 'Top Shelf' is a commercial blueberry variety intended for the hand harvest market.

PLANT

Plant size: Medium.
- *a. Height of plant.*—Average of 34 inches on 3 year old plants.
- *b. Canopy diameter.*—Average of 37 inches on 3 year old plants.

Growth habit: Upright, vase shaped.
Plant vigor: Vigorous.
Twigginess: Low.
Evergreenness: Deciduous.
Suckering: Low.
Chilling requirement: Approximately 700 to 1000 hours.
Cold hardiness: Approximately USDA zones 6-8.
Productivity in Lowell, Oreg.:
- *a. 2 year old plants.*—Average of 3.4 lbs per plant, compared to 2.3 lbs per plant on Draper plants of the same age.
- *b. 3 year old plants.*—Average of 4.5 lbs per plant, compared to 4.1 lbs per plant on Draper plants of the same age.

Propagation: Easy to propagate from softwood cuttings.
Disease and pest resistance/susceptibility:
- *a. Root rot* (*Phytophthora cinnamomi*).—Does not appear to be overly susceptible.
- *b. Stem blight* (*Botryosphaeria spp*).—Undetermined.
- *c. Phomopsis twig blight* (*Phomopsis vaccinii*).—Does not appear to be overly susceptible.
- *d. Botryosphaeria stem canker* (*Botryosphaeria corticis*).—Undetermined.
- *e. Bacterial cane canker* (*Pseudomonas syringae*).—Does not appear to be overly susceptible.
- *f. Botrytis blight* (*Botrytis cinerea*).—Does not appear to be overly susceptible.
- *g. Leaf spot* (*Septoria spp.*).—Does not appear to be overly susceptible.
- *h. Leaf rust* (*Naohidemyces vaccinii*).—Does not appear to be overly susceptible.
- *i. Bud mites* (*Acalatus vaccinii*).—Undetermined.

Disease survival: Good.

TRUNK AND BRANCHES

Texture:
- *a. Surface texture new wood.*—Smooth.
- *b. Surface texture 1 yr wood.*—Smooth.
- *c. Surface texture 3 yr wood.*—Rough.

Color:
- *a. Color of new wood.*—Pantone colors Sweet Pea 15-0531 and *Chrysanthemum* 17-1641.
- *b. Color of rough bark at 1 year.*—Pantone colors Mineral red 17-1537 and Green Banana 14-0434.
- *c. Color of rough bark 3 years.*—Pantone colors Sesame 15-1215, Almond 16-1432, Mineral Red 17-1537.

FOLIAGE

Internode length: Average of 21.55 mm.
Leaf dimensions:
- *a. Leaf length.*—Average of 73.6 mm.
- *b. Leaf width.*—Average of 43.6 mm.

Leaf shape: Elliptical.
Leaf margin: Entire.
Leaf color:
- *a. Upper leaf surface.*—Pantone color Chive 19-0323. Some leaves with a Brown stone 19-1322 accent.
- *b. Lower leaf surface.*—Pantone color Epsom 17-0324.

Fall foliage color: Pantone Maroon 18-1619.
Pubescence:
- *a. Pubescence upper leaf surface.*—Absent.
- *b. Pubescence lower leaf surface.*—Absent.
- *c. Pubescence leaf margins.*—Absent.

Petiole:
- *a. Petiole length.*—Average of 3.71 mm.
- *b. Petiole color.*—Pantone color Moss 16-0532.
- *c. Petiole surface texture.*—Smooth.

Precocity: In Lowell, Oreg. flower bud break occurs prior to vegetative bud break. Flowers persist during initial vegetative growth period.

FLOWERS

Flower arrangement: Alternate arrangement.
Anther:
- *a. Anther length.*—Average of 4.54 mm.
- *b. Anther color.*—Pantone color Burnt Orange 16-1448.

Immature flower color: Pantone colors Lilac Rose 17-2227 and Snow white 11-0602.
Fragrance: Faint.
Stigma location: Average 0.31 mm below lip of corolla.
Flower shape: Urceolate to cylindrical.
Pollen:
- *a. Pollen staining.*—Approximately 95% viable, Staining with 2% acetocarmine dye.
- *b. Pollen abundance.*—Medium.
- *c. Pollen color.*—Pantone color Pale Banana 12-0824.

Flower length: Average of 12.38 mm.

Corolla:

*a. Corolla length*.—Average of 8.68 mm.

*b. Corolla diameter*.—Average of 8.21 mm.

*c. Corolla aperture*.—Average of 5.53 mm.

*d. Corolla color*.—Pantone color Snow White 11-0602.

*e. Corolla texture*.—Smooth.

Style length: Average of 8.40 mm.

Calyx:

*a. Calyx diameter*.—Average of 5.60 mm.

*b. Calyx surface*.—Smooth.

*c. Calyx color*.—Pantone color Spinach Green 16-0439, lobes Lettuce Green 13-0324 and Red Violet 17-1818.

Pistil color: Pantone colors Peridot 17-0336 and Herbal garden 15-0336.

Flower pedicel:

*a. Pedicel color*.—Pantone color Spinach green 16-0439 and Red Violet 17-1818.

*b. Pedicel length*.—Variable, average of 8 mm.

Flower peduncle:

*a. Peduncle color*.—Pantone colors Apple green 15-0543 and Catchup 18-1449.

*b. Peduncle length*.—Average of 24.51 mm.

Flowering period: Late April through late May in Lowell, Oreg.

Flowering cluster: Loose.

Number of flowers: Average of 6-8 flowers per cluster.

Self-compatibility: Good. On average 81% of self-pollinated flowers reach maturity.

Average inflorescence size: 32.5 mm.

FRUIT

Mean harvest date: July 25.

Mean date last pick: August 15.

Calyx:

*a. Calyx aperture*.—Average of 6.65 mm.

*b. Calyx lobes*.—5 lobes, not well defined.

*c. Calyx depth*.—Average of 2.11 mm. Pistils tend to remain on berries until after harvest, when most fall off.

Berry cluster: Moderately tight, does not misshape fruit.

Berry pedicel:

*a. Pedicel length*.—Average of 6.98 mm.

*b. Pedicel surface texture*.—Smooth.

Berry peduncle:

*a. Peduncle length*.—Average of 21.37 mm.

*b. Peduncle surface texture*.—Smooth.

Berries per cluster: Average of 7 to 8 berries per cluster.

Berry detachment: Easy.

Berry weight: Average berry weight of 3.24 g, compared to Draper plants of the same age, which have an average berry weight of 2.58 g.

Berry height: Average of 13.85 mm.

Berry width: Average of 20.86 mm.

Berry shape: Oblate.

Berry color:

*a. Immature berry color*.—Pantone color Green Olive 17-0535.

*b. Berry skin color on plant*.—Pantone color Lilac Gray 14-3903.

*c. Berry skin color after harvest*.—Pantone color Purple Cloud 16-3919.

*d. Berry skin color after polishing*.—Pantone color Dark Navy 19-0413.

Berry wax: Moderately heavy & moderately persistent.

Berry flesh color: Pantone color Celery Green 13-0532.

Pedicel scar: Average of 3.02 mm in diameter.

Berry firmness: Very good. Average berry firmness measurement for Top Shelf is 223 g/mm of deflection, compared to Draper plants harvested on the same day, which have an average of 223 g/mm of deflection, as measured by a Firmtech fruit firmness testing machine.

Berry flavor: Mildly sweet.

Berry texture: Firm.

SEEDS

Seed color: Pantone color Mahogany 18-1425.

Seed length: Average of 1.25 mm.

Seed width: Average of 0.87 mm.

Seed weight: Average of 0.2 mg.

Quantity seeds per berry: Average of 58 seeds per berry.

TABLE 1

DISTINGUISHING FEATURES FROM FEMALE PARENT 'MAGNOLIA'

| Name of maternal parent | Characteristic(s) in which the candidate variety differs from the maternal parent | Describe the expression of the characteristic for the maternal parent | Describe the expression of the characteristic for 'Top Shelf' |
|---|---|---|---|
| Magnolia | Chilling requirement | 500 hours below 45 degrees Fahrenheit | 700-1000 hours below 45 degrees Fahrenheit |
| Magnolia | Growth habit | Spreading | Vase shaped, upright |

The invention claimed is:

1. A new and distinct variety of blueberry plant named 'Top Shelf,' substantially as illustrated and described herein.

* * * * *